(12) United States Patent
Emans et al.

(10) Patent No.: US 8,962,666 B2
(45) Date of Patent: Feb. 24, 2015

(54) METHOD FOR IMPROVING CARTILAGE REPAIR AND/OR PREVENTING CARTILAGE DEGENERATION IN A JOINT

(71) Applicants: Maastricht University, Maastricht (NL); Academic Hospital Maastricht, Maastricht (NL)

(72) Inventors: Peter Joseph Emans, Maastricht (NL); Lodewijk Willem Van Rhijn, Maastricht (NL); Tim Johannes Maria Welting, Klimmen (NL); Mike De Leeuw, Mheer (NL)

(73) Assignees: Maastricht University, Maastricht (NL); Academic Hospital Maastricht, Maastricht (NL)

( * ) Notice: Subject to any disclaimer, the term of this patent is extended or adjusted under 35 U.S.C. 154(b) by 27 days.

(21) Appl. No.: 13/677,071

(22) Filed: Nov. 14, 2012

(65) Prior Publication Data
US 2013/0123314 A1    May 16, 2013

Related U.S. Application Data

(62) Division of application No. 12/709,169, filed on Feb. 19, 2010, now abandoned.

(60) Provisional application No. 61/154,328, filed on Feb. 20, 2009.

(51) Int. Cl.
| | |
|---|---|
| *A61K 31/42* | (2006.01) |
| *A61K 31/40* | (2006.01) |
| *A61K 9/00* | (2006.01) |
| *A61K 31/728* | (2006.01) |
| *A61L 27/52* | (2006.01) |
| *A61L 27/54* | (2006.01) |
| *A61K 38/20* | (2006.01) |

(52) U.S. Cl.
CPC ............ *A61K 9/0019* (2013.01); *A61K 9/0024* (2013.01); *A61K 31/42* (2013.01); *A61K 31/728* (2013.01); *A61L 27/52* (2013.01); *A61L 27/54* (2013.01); *A61K 38/2013* (2013.01); *A61L 2300/252* (2013.01); *A61L 2300/414* (2013.01); *A61L 2300/426* (2013.01); *A61L 2300/432* (2013.01); *A61L 2300/452* (2013.01)
USPC .......................................................... 514/378

(58) Field of Classification Search
CPC ...... A61K 9/0019; A61K 31/42; A61K 31/40
USPC .......................................................... 514/378
See application file for complete search history.

(56) References Cited

U.S. PATENT DOCUMENTS

2009/0269406 A1 * 10/2009 Panitch et al. ................ 424/487

OTHER PUBLICATIONS

Jean YH. et al. "Intra-articular injection of the cyclooxygenase-2 inhibitor parecoxib attenuates osteoarthritis progression in anterior cruciate ligament-transected knee in rats: role of excitatory amino acids". OsteoArthritis and Cartilage (2007) 15, 638-645.*
Neustadt DH. "Intra-articular injections for osteoarthritis of the knee". Cleveland Clinic Journal of Medicine vol. 73, No. 10, Oct. 2006, pp. 897-911.*
Fortier et al, "The Role of Growth Factors in Cartilage Repair", Clin. Orthop, Relat. Res. 469:2706-2715 (2011).
Davidson et al, "TGF-β and osteoarthritis", OsteoArthritis and Cartilage 15:597-604 (2007).
Yoshimura et al, "Transforming growth factor-β stimulates IL-1β-induced monocyte chemoattractant protein-1 expression in human synovial cells via the ERK/AP-1 pathway", Inflamm. Res. 55:543-549 (2006).

* cited by examiner

*Primary Examiner* — Renee Claytor
(74) *Attorney, Agent, or Firm* — Nixon & Vanderhye P.C.

(57) ABSTRACT

The invention is in the field of methods for medical treatment. It provides an improved method for repairing damaged cartilage and/or preventing cartilage degeneration in tissue, in particular in a joint by administering a pharmaceutically active agent directly into the fat pad of a joint. The pharmaceutically active agent is preferably selected from the group consisting of agents that stimulate chondrogenic differentiation and/or cartilage matrix synthesis; agents that inhibit osteogenesis and/or hypertrophy, anti-inflammatory agents, agents that inhibit apoptosis of chondrocytes, agents that inhibit senescence of chondrocytes and agents that enhance lubrication of a joint.

8 Claims, 2 Drawing Sheets

FIGURE 1

Fat Pad

FIGURE 2

METHOD FOR IMPROVING CARTILAGE REPAIR AND/OR PREVENTING CARTILAGE DEGENERATION IN A JOINT

This application is a divisional of U.S. application Ser. No. 12/709,169, filed Feb. 19, 2010, which claims priority from U.S. Provisional Application No. 61/154,328 filed Feb. 20, 2009, the entire contents of each of which are hereby incorporated by reference.

FIELD OF THE INVENTION

The invention is in the field of methods for medical treatment. It provides an improved method for repairing damaged cartilage and/or preventing cartilage degeneration and/or managing pain in tissue, in particular in a joint.

BACKGROUND OF THE INVENTION

During our life moving, walking, sport, etc. is essential for our health and quality of life. We fully depend on joint motion for these abilities. The presence of healthy articular cartilage is essential for joint motion. Articular cartilage is exposed to an enormous amount of intensive and repetitive forces during life. The wear resistance and friction modus of articular cartilage are unique, however when damaged, cartilage has a limited capacity for regeneration. Articular cartilage lesions which fail to heal spontaneously eventually evolve in osteoarthritis (OA)[3, 6, 7].

OA is among the most frequent forms of musculoskeletal disorders affecting over 10% of the adult population[9]. While primary osteoarthritis (OA) is defined as joint degeneration without any underlying cause, in secondary OA joint degeneration is often caused by trauma (e.g. during sports or in traffic accidents). Traumatic cartilage lesions can be asymptomatic, the percentage of individuals suffering from OA due to a trauma is unknown and may be underestimated. From literature it is known that sixteen to twenty percent of patients with a traumatic hemarthros have a cartilage defect[4, 8], and even up to 60% of patients undergoing a arthroscopy have a cartilage defect[1, 2, 5]. OA is a significant socio-economic burden and recent developments for treatment of OA have led to an increasing interest for this affection. Together with rheumatoid arthritis (RA) OA is the most common cause of articular cartilage degeneration.

Many factors have been described to influence cartilage repair and prevent cartilage degeneration. A growing number offers a number of bioactive reagents, including pharmaceutically active agents, proteins (e.g. growth factors) and nucleic acids and can be administered and targeted as such or by using gene-transfer approaches and RNAi, US 2008269762 A1 relates to a method for treating a cartilage defect in a human subject comprising the steps of obtaining blood compatible with the subject, fractionating said blood to produce platelet-poor plasma, concentrating said platelet-poor plasma to produce a platelet-poor plasma concentrate and administering said concentrate to the site of said cartilage defect.

US 2008274157 A1 describes a method of placing a preshaped allograft implant assembly in a cartilage defect, said assembly comprising a subchondral bone and an overlying cartilage cap plug which has been treated to remove cellular debris and proteoglycans and minced cartilage in a carrier comprising the steps of: (a) drilling a cylindrical hole in a patient at a site of a cartilage defect to a depth which equal to or less than the length of the bone and cartilage cap plug implant to be placed therein forming a blind bore; (b) placing a preshaped osteochondral plug having a cross section which is less than the cross sectional area of the bore with a gap between the exterior surface of the plug and at least one side wall defining the drilled bore being less than 2 mm allowing the implant to be laterally moveable within said bore in the cylindrical hole; (c) mixing minced allograft cartilage in a fibrinogen thrombin solution; and (d) placing the minced cartilage in fibrinogen thrombin solution in the gap between the plug and at least one side wall defining the bore and allowing the cartilage and solution to polymerize.

US 2008269895 A1 is concerned with an implant suitable for the repair of a cartilage defect in a human or animal subject, which implant comprises an implant body including a natural cartilage matrix produced by in vitro tissue culturing from cells or produced from ex vivo cartilage tissue and which implant further comprises viable cells having a chondrogenic potential and adhered to the surface of the implant body.

Jean et al. (OsteoArthritis and Cartilage (2007) 15, 638-645) describes the effect of intra-articular injection of the cyclooxygenase-2 (COX-2) inhibitor parecoxib on osteoarthritis (OA) progression. Parecoxib alone did not have any effect on cartilage and synovium of normal knees in naive rats. In anterior cruciate ligament-transected (ACLT) knees, parecoxib showed significant inhibition of cartillage degeneration. Intra-articular parecoxib injection suppressed synovial inflammation, and glutamate and aspartate levels were reduced as well. This shows that intra-articular injection of a COX-2 inhibitor inhibits ACLT-induced OA progression.

US 2008262618 A1 provides a prosthesis device, comprising: a body at least partly formed from a segmented thermoplastic elastomer having crystallized blocks, and having at least one functional component which is able to reversibly bond to the crystallized blocks, wherein the elastomer has cartilage regenerative properties.

WO 2008122595 A2 relates to an at least partially biodegradable implant suitable for implantation into a subject for repairing a bone or cartilage defect, comprising: a matrix of a non-particulate material, the matrix having an open-celled structure having a plurality of interconnected spaces, and a plurality of particles of a metallic material, wherein the spaces in the matrix are substantially completely filled with the metallic material particles, and wherein at least one of the metallic material or the matrix material is at least partially degradable in-vivo.

EP 1932536 A2 discloses a collagenase composition for the treatment of soft tissue, wherein the treatment comprises applying the collagenase composition to a defect or injury in soft tissue in a patient, thereby promoting healing of the defect or injury.

SUMMARY OF THE INVENTION

The invention is based on the discovery that a fat pad that is naturally present in human and animal joints is a suitable depot for the controlled and/or delayed release of pharmaceutical compounds. This may advantageously be employed in the treatment of diseases of the joint, in particular for improving cartilage repair and/or the prevention of cartilage degeneration The invention therefore relates to a method for improving cartilage repair and/or slowing down of cartilage degeneration or the prevention of further cartilage degeneration by administering a pharmaceutically active agent directly into the fat pad of a joint. The invention also relates to an improved method of administrating pain-killers for articular joint pain.

This invention also describes a method that offers protection of the targeted tissues against overdosing and cytotoxicity as a consequence of injecting a drug depot of concentrated drugs-formulation, by packaging the drugs inside a biodegradable injectable polymer that will slowly release the enclosed drugs

DETAILED DESCRIPTION OF THE INVENTION

We discovered that an active pharmaceutical agent is retained at the application site when injected into the infrapatellar fat pad of a human or animal joint, resulting in a superior treatment of medical conditions of the joint.

The infrapatellar fat pad (sometimes known as Hoffa's pad) is a soft tissue that lies beneath the patella (kneecap) separating it from the femoral condyle (end of the thigh bone). In situations where forces are directed at the patella it acts as a shock absorber, thus protecting the underlying structures.

The infrapatellar fat pad is an intracapsular structure that may be visualized on magnetic resonance images of the knee. As the fat pad of Hoffa is primarily composed of structural fat tissue that is not strongly influenced by nutrition, it is conjectured that the pad may have bio-mechanical behavior (e.g. cushioning) in addition to energy storage.

Abnormalities in bio-mechanical function have been attributed to infrapatellar knee pathology. For example, variations in the dorsal contour of infrapatellar fat pad including indentations can frequently be observed. Amongst recent work on the analysis of medical images of Hoffa, Ozkur et al studied the prevalence and the shape of a fluid-like indentation, a recess, at the inferior posterior margin of Hoffa's fat pad from MR image examinations of the knee. They examined the location, size and morphology of the recess visually and using calipers and performed statistical analysis between patients with and without a recess and correlated this with the incidence of joint effusion.

The present invention is not concerned with such abnormalities of the fat pad but is rather directed at delivery of pharmaceutical agents to the otherwise healthy fat pad in order to treat diseases and injuries of the joint other than fat pad related diseases.

The following is provided as non-limiting examples of diseases, injuries and cartilage repair strategies that may be treated with the present invention; Osteoarthritis (OA), Rheumatoid Arthritis (RA) and related inflammatory diseases such as gout and pseudogout, juvenile arthritis, psoriatic arthritis etc., infections (e.g. caused by bacteria, viruses etc.), hoffitis, patellofemoral pain, patellar chondropathy and cartilage lesions (e.g. caused by a trauma or Osteochondrotis Dissecans (OCD) and the treatment of such cartilage lesions (e.g. mosaic plasty, biomaterial/scaffold implantation with or without cells and or growthfactors, exercise therapy, Continues Passive Motion (CPM), Joint distraction, correction osteotomy, microfracture, abrasion therapy, Autologous Chondrocyte Transplantation (ACT), Matrix Assisted Chondrocyte Implantation (MACI) or cartilage xenograft techniques.

One of the key features of joint failure or joint pain is cartilage degeneration. The invention addresses that problem by providing a method for improving cartilage repair and/or the prevention of cartilage degeneration by administering a pharmaceutically active agent directly into the fat pad of a joint. The term joint related pain as used herein refers to pain that originates from cartilage degeneration of the joint.

The term "pharmaceutically active agent" includes a "drug" and means a molecule, group of molecules, complex or substance administered to an organism for diagnostic, therapeutic, preventative medical, or veterinary purposes. This term includes human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA), ribonucleic acid (RNA), or mixtures or combinations thereof, including, for example, DNA nanoplexes, antisense molecules, aptamers, ribozymes, triplex forming molecules, PNA, RNAi, siRNA and external guide sequences.

Pharmaceutically active agents include the herein disclosed categories and specific examples. It is not intended that the category be limited by the specific examples. Examples include a radiosensitizer, a steroid, a xanthine, an anti-inflammatory agent, an analgesic agent, an anticoagulant agent, an antiplatelet agent, a sedative, an antineoplastic agent, an antimicrobial agent, an antifungal agent, a protein, or a nucleic acid.

Thus, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; anti-inflammatory agents, including antiasthmatic anti-inflammatory agents, anti-arthritis anti-inflammatory agents, and non-steroidal anti-inflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen celecoxib and piroxicam; analgesic agents such as salicylates; anticoagulant and antiplatelet agents such as coumadin, warfarin, acetylsalicylic acid, and ticlopidine; sedatives such as benzodiazapines and barbiturates; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; antimicrobial agents such as penicillins, cephalosporins, and macrolides, antifungal agents such as imidazolic and triazolic derivatives; and nucleic acids such as DNA sequences encoding for biological proteins, peptides and antisense oligonucleotides Cartilage repair and/or prevention of cartilage degeneration may be achieved via a number of different mechanisms.

More specifically, useful pharmaceutically active agents to be used in the invention may be factors that stimulate chondrogenic differentiation and cartilage matrix synthesis, such as compounds selected from the group consisting of TGF-β-1,2, and 3, BMP-2-4-7, CDMP, GDF-5, IGF-1, FGF family, SMAD-1, -2, -3, -4, -5, -6, -7, -8, EDF, PDGF, type II collagen, type IX collagen, cartilage-link protein, COMP, GlcAT-1, SOX5, SOX6, SOX9, MEF2C, DIx5, Nkx2.5, PTHrP, Ihh, Wnt, CTGF, collagen hydrolysate.

Hence, the invention relates to a method as described above wherein said pharmaceutically active agents are selected from the group consisting of Growth factors, TGF-β-1,2, and 3, BMP-2-4-7, CDMP, GDF-5, IGF-1, FGF family, SMAD-1,-2,-3-4,-5,-6,-7,-8, EDF, PDGF, type II collagen, type IX collagen, cartilage-link protein, COMP and GIcAT-1, SOX5, SOX6, SOX9, MEF2C, DIx5, Nkx2.5, PTHrP, Ihh, Wnt, CTGF.

A "growth factor" includes any soluble factor that regulates or mediates cell proliferation, cell differentiation, tissue regeneration, cell attraction, wound repair and/or any developmental or proliferative process. For example, fibroblast growth factor-2 (FGF-2), fibroblast growth factor-1 (FGF-1), epidermal growth factor (EGF), heparin binding growth factor (HBGF), Placental Growth Factor (PIGF), vascular endothelial growth factor (VEGF), transforming growth factor-alpha (TGF-.alpha.), transforming growth factor-beta (TGF-.beta.), insulin-like growth factor (IGF-I, IGF-II), platelet derived growth factor (PDGF), leukemia inhibitory factor (LIF), and platelet rich plasma (PRP).

Also, useful pharmaceutically active agents may be agents that inhibit osteogenesis and/or hypertrophy. Such agents may be selected from the group consisting of noggin, chordin, PTHrP, lhh, Shh, DHH, Smad 6, 7, mIAP-1 and COX-1 and COX-2 inhibitors.

Hence, the invention relates to a method wherein said agents that inhibit osteogenesis and/or hypertrophy are selected from the group consisting of noggin, chordin, PTHrP, lhh, Shh, DHH, Smad 6, 7, mIAP-1 and COX-1 and COX-2 inhibitors.

Also, useful pharmaceutically active agents may be anti-inflammatory agents or agents that enhance the outcome of cartilage regenerative techniques. Such agents may be selected from the group consisting of II-1 Ra, sIL-1R, ICE inhibitor, sTNFR, anti-TNF-antibodies, TACE inhibitor, TIMP-1,-2, MMP inhibitors, II-4, -6, -8, -10, -11, 13, GFAT, NFkB, COX-1 and COX-2 inhibitors.

Hence, the invention relates to a method wherein said anti-inflammatory agents are selected from the group consisting of II-1 Ra, sIL-1R, ICE inhibitor, sTNFR, anti-TNF-antibodies, TACE inhibitor, TIMP-1,-2, MMP inhibitors, II-4, -6, -8, 10, -11, 13, GFAT, NFkB, COX-1 and COX-2 inhibitors.

Hence, the invention relates to a method wherein said agents may improve the outcome of cartilage regenerative techniques wherein said techniques may be ACT, MACI, microfracture, OATS or cartilage xenograft techniques.

Also, useful pharmaceutically active agents may be agents that can reduce pain as experienced in various diseases such as RA, OA and trauma of the cartilage. Such agents may be selected from the group consisting of pain killers known in the art.

Hence, the invention relates to a method wherein said agents may reduce pain and suffering as a consequence of degeneration or trauma of cartilage, or as a consequence of operations to the joints.

Also, useful pharmaceutically active agents may be agents that inhibit apoptosis of chondrocytes. Such agents may be selected from the group consisting of Bcl-2, Bcl-XL, Smad-7, anti-FasL, Akt, PI-3-kinase, NFkB and hyaluronan.

Hence, the invention relates to a method wherein said agents that inhibit apoptosis of chondrocytes are selected from the group consisting of Bcl-2, Bcl-XL, Smad-7, anti-FasL, Akt, PI-3-kinase, NFkB and hyaluronan.

Also, useful pharmaceutically active agents may be agents that inhibit senescence of chondrocytes. Such agents may be selected from the group consisting of hTERT, NO (iNOS) antagonist and SOD.

Hence, the invention relates to a method wherein said agents that inhibit apoptosis of chondrocytes are selected from the group consisting of hTERT, NO (iNOS) antagosnist and SOD.

Also, useful pharmaceutically active agents may be that enhance lubrication of a joint. Such agents may be selected from the group consisting of hyaluronan and superficial zone protein (SZP)/lubricin.

Hence, the invention relates to a method wherein said agents that enhance lubrication of a joint are selected from the group consisting of hyaluronan and superficial zone protein (SZP)/lubricin.

It should be understood that the cartilage defect may be in any joint of a human subject or animal subject, including shoulders, elbows, wrists, ankles, hips, and the spinal column, in which cartilage tissue is inadequate for physiological or cosmetic purposes. In this regard, cartilage defects include congenital cartilage defects, cartilage defects that result from or are symptomatic of disease, disorder, or trauma, and cartilage defects that are consequent to surgical or other medical procedures.

For example, cartilage defects may be defects resulting from osteoporosis, spinal fixation procedures, hip and other joint replacement procedures, and chronic wounds.

The pharmaceutically active agents may be delivered to the fat pad by any method and/or in any form. Preferred delivery forms are injection through a needle or implantation through surgery; incision of the skin, through or next to the patella-tendon and opening of the joint capsule.

The form in which the pharmaceutically active agent is delivered is also not critical. It may be in solution or in solid form. Preferably however, it is delivered in the context of a device suitable for controlled release of said agent, such as a gel.

The invention therefore relates to a method as described above wherein said pharmaceutically active agent is contained in a device suitable for controlled release of said agent.

A gel (from the latin gelu—freezing, cold, ice or gelatus—frozen, immobile) is a solid, jelly-like material that can have properties ranging from soft and weak to hard and tough. Gels are defined as a substantially dilute crosslinked system, which exhibits no flow when in the steady-state. By weight, gels are mostly liquid, yet they behave like solids due to a three-dimensional crosslinked network within the liquid. It is the crosslinks within the fluid that give a gel its structure (hardness) and contribute to stickiness (tack).

A particularly suitable gel is a biogel. A "biogel" is a gel that is compatible with biological systems. That means, a biogel is a gel that does not interfere negatively with the particular biological system. A biogel is a gel that delivers biological active components to a biological system or forms the active components by its own breakdown products. A biogel is a gel that may be biodegradable. Biodegradability implies that the gel actively or passively degrades in the particular biological system.

The invention therefore relates to a method as described above wherein said device is a biogel comprising a biocompatible polymer.

A solid three-dimensional network spans the volume of a liquid medium. This internal network structure may result from physical or chemical bonds, as well as crystallites or other junctions that remain intact within the extending fluid. Virtually any fluid can be used as an extender including water (hydrogels), oil, and air (aerogel). Both by weight and volume, gels are mostly liquid in composition and thus exhibit densities similar to those of their constituent liquids.

One example of gel constituents suitable in the invention are cationic polymers which are positively charged polymers. Their positive charges prevent the formation of coiled polymers. This allows them to contribute more to viscosity in their stretched state, because the stretched-out polymer takes up more space than a coiled polymer and this resists the flow of solvent molecules around it. Suitable examples are for instance a copolymer of vinylpyrrolidone, methacrylamide, and hydrogel N-vinylim idazole.

Another example of suitable gels are hydrogels. A hydrogel (also called aquagel) is a network of polymer chains that are water-insoluble, sometimes found as a colloidal gel in which water is the dispersion medium. Hydrogels are superabsorbent (they can contain over 99% water) natural or synthetic polymers. Hydrogels also possess a degree of flexibility very similar to natural tissue, due to their significant water content.

The term "(hydro)gel," refers to a network of polymer chains that are water-soluble, sometimes found as a colloidal gel in which water is the dispersion medium. Hydrogels can be superabsorbent natural or synthetic polymers. For example, hydrogels can contain over 99% water. Hydrogels can also possess a degree of flexibility very similar to natural tissue, due to their significant water content. However, it is also understood that in one aspect, the disclosed hydrogels can comprise water or water mixed with other miscible liquids, for example, alcohols.

Hydrogels can comprise positively charged, negatively charged, and neutral hydrogels that can be saturated or unsaturated. Examples of hydrogels are TETRONICS™, and POLOXAMINES™ which are poly(oxyethylene)-poly(oxypropylene) block copolymers of ethylene diamine; polysaccharides, chitosan, poly(vinyl amines), poly(vinyl pyridine), poly(vinyl imidazole), polyethylenimine, poly-L-lysine, growth factor binding or cell adhesion molecule binding derivatives, derivatised versions of the above (e.g. polyanions, polycations, peptides, polysaccharides, lipids, nucleic acids or blends, block-copolymers or combinations of the above or copolymers of the corresponding monomers); agarose, methylcellulose, hydroxyproylmethylcellulose, xyloglucan, acetan, carrageenan, xanthan gum/ocust beangum, gelatine, collagen particularly Type 1), PLURONICS™, POLOXAMERS™, Poly(N-isopropylacrylmide) and N-isopropylacrylmide copolymers. Thus, for example, the polymer can comprise a saccharide residue, an ethylene oxide residue, a propylene oxide residue, an acrylamide residue, or a blend or copolymer thereof. Thus, the polymer can be agarose. The polymer can be a polaxomers, or a derivative thereof. The polymer can be a polyacrylamides, or a derivative thereof. The polymer can be N-isopropylacrylamide (NIPAM), or a derivative thereof. The polymer can be Pluronic F127, or a derivative thereof.

Other examples of hydrogels useful in the proposed method of treatment are the so-called stereo-complexed hydrogels as described in patents WO0048576/WO2005054318/WO 2008/018796 by W. H. Hennink et al.

Other examples of hydrogels useful in the proposed method of treatment are gels based on charged particles as described in the patent WO2005110377 by W. E. Hennink et al Other examples of hydrogels useful in the proposed method of treatment are gels based on non PEG-containing Thermo Reversible Hydrogels as described in the patent WO 2009/037313 A1 by J. Heller et al Other examples of hydrogels useful in the proposed method of treatment are gels based on Thermo reversible Gels containing aliphatic side chains as described in patent US 2007/0265356 A1 by S. W. Kim et al Other examples of hydrogels useful in the proposed method of treatment are gels based on Thermo reversible Gels containing aliphatic side chains as described in patent GAMMA II by S. J. Pierre et al An advantage of the herein disclosed biocompatible hydrogels is that they do not require the addition of exogenous cells, such as chondrocytes. Thus, the biocompatible hydrogel can be substantially free of exogenous cells. For example, the biocompatible hydrogel can be substantially free of exogenous chondrocytes, osteoblasts, mesenchymal stem cells (MSC), pluripotent stem cells, hematopoeitic, dermal stem cells, and myoblasts prior to implantation. As used herein, exogenous cells are cells that are added to the gel ex vivo and thus can include autologous and heterologous cells. However, it is understood that the biocompatible hydrogel can comprise endogenous, autologous cells (e.g., chondrocytes and cartilage cells) that migrate into said gel after implantation.

The biocompatible hydrogel can comprise at least about 0.1%, at least about 0.5%, at least about 1%, at least about 2%, at least about 3%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% of the polymer by weight.

Hydrogels are commonly used as scaffolds in tissue engineering. When used as scaffolds, hydrogels may contain human cells in order to repair tissue.

Hydrogels may also be used as sustained-release delivery systems. They provide for absorption, desloughing and debriding capacities of necrotics and fibrotic tissue.

Hydrogels are known as reservoirs in topical drug delivery; particularly ionic drugs, delivered by iontophoresis. Common ingredients are e.g. polyvinyl alcohol, sodium polyacrylate, acrylate polymers and copolymers with an abundance of hydrophilic groups. Natural hydrogel materials are being investigated for tissue engineering, these materials include agarose, methylcellulose, hylaronan, and other naturally derived polymers.

The term "gels" also includes organogels. An organogel is a non-crystalline, non-glassy thermoreversible (thermoplastic) solid material composed of a liquid organic phase entrapped in a three-dimensionally cross-linked network. The liquid can be e.g. an organic solvent, a mineral oil or a vegetable oil. The solubility and particle dimensions of the structurant are important characteristics for the elastic properties and firmness of the organogel. Often, these systems are based on self-assembly of the structurant molecules.

The term Biogel refers for example to a hydrogel, a micro-nanosphere or liposome as described above with the distinct property that it disintegrates from its original form and functional properties to degrade to sub-fragments of the original chemical and physical composition. This disintegration occurs over time due to hydrolytic and/or enzymatic activity and/or mechanical activity within the mammalian body, and can be removed from the body either via excretion and or metabolic activity.

The term "biogels" also includes saccharide Polymers: The saccharide residues of the polymer can be monosaccharides, disaccharides, or polysaccharides. The saccharide residues of the polymer can exists in the form of a pyranose or furanose (6 or 5 member rings). The saccharide residues of the polymer can be galactose sugars. The saccharide residues of the polymer can comprise .alpha.1.fwdarw.4, .beta. 1.fwdarw.3 glycosidic linkages. At least a portion of the saccharide residue of the polymer can have .alpha.(1.fwdarw.4)-.alpha. and (1.fwdarw.3)-.beta. glycosidic bond.

The saccharide residues of the polymer can be lecithin, amylase, amylopectin, mannose residues, N-acetyl glucosamine, N-acetyl galactosamine, or fucose. The saccharide residues of the polymer can be O-linked or N-linked glycans. The saccharide residues of the polymer can be heparin sulfate, Dermatan sulfate, Chondroitin sulfate, or other proteoglycans. The polymer can be a linear polymer. The polymer can be a sugar derivatized polymer. The polymer can be a hyper branched star polymer. The polymer can be a dendrimer. The polymer can be a graft polymer The term "biogel" also includes agarose, i.e. at least one polymer can be agarose or a derivative thereof. The polymer can be a carrageenan or a derivative thereof. Agarose is an extract of agar, which consists of a mixture of agarose and agaropectin. Agar is prepared from red seaweed (Rhodophycae) and is commercially obtained from species of Gelidium and Gracilariae.

Agaropectin is a heterogeneous mixture of smaller molecules that occur in lesser amounts. Their structures are similar but slightly branched and sulfated, and they may have methyl and pyruvic acid ketal substituents. They gel poorly and may be simply removed from the excellent gelling agarose molecules by using their charge.

Agarose is a linear polymer, of molecular weight about 120,000, based on the -(13)-.beta.-D-galactopyranose-(14)-3,6-anhydro-.alpha.-L-galactopyranos-e unit.

Thus, the polymer can comprise poly(1.fwdarw.4)-3,6-anhydro-.alpha.-L-galactopyranosyl-(1.fwdarw.3)-.bet-a.-D-galactopyranan. The polymer can comprise alternating .beta.-(1.fwdarw.3)-D and .beta.-(1.fwdarw.4)-L linked galactose residues. Agarose molecules have molecular weights about 120,000, The gel network of agarose contains double helices formed from left-handed threefold helices. These double helices are stabilized by the presence of water molecules bound inside the double helical cavity. Exterior hydroxyl groups allow aggregation of up to 10,000 of these helices to form suprafibers. Thus, the polymer can comprise at least two strands that form a double helix stabilized by the presence of water molecules inside the helix. The polymer can comprise exterior hydroxyl groups that allow aggregation of the helices into fibers.

The polymer can also be a carrageenan or a derivative thereof. Carrageenan is a collective term for polysaccharides prepared by alkaline extraction (and modification) from red seaweed (Rhodophycae), mostly of genus *Chondrus, Eucheuma, Gigartina* and *Iridaea*. Different seaweeds produce different carrageenans. Carrageenans are linear polymers of about 25,000 galactose derivatives with regular but imprecise structures, dependent on the source and extraction conditions. The major differences between agarose and carrageenans being the presence of L-3,6-anhydro-.beta.-galactopyranose rather than D-3,6-anhydro-.alpha.-galactopyranose units and the lack of sulfate groups. The idealized structure of .kappa.-carrageenan (kappa-carrageenan) is: -(1.fwdarw.3)-.beta.-D-galactopyranose-4-sulfate-(1.fwdarw.4)-3,6-an-hydro-.alpha.-D-galactopyranose-(1.fwdarw.3). Arrageenan is produced by alkaline elimination from .mu.-carrageenan isolated mostly from the tropical seaweed *Kappaphycus alvarezii* (also known as *Eucheuma cottonii*). The experimental charge/dimer is 1.03 rather than 1.0 with 0.82 molecules of anhydrogalactose rather than one. The idealized structure of -carrageenan (iota-carrageenan) is:— (1.fwdarw.3)-.beta.-D-galactopyranose-4-sulfate-(1.fwdarw.4)-3,6-anhydr-o-.alpha.-D-galactopyranose-2-sulfate-(1.fwdarw.3). Carrageenan is produced by alkaline elimination from v-carrageenan isolated mostly from the Philippines seaweed *Eucheuma denticulatum* (also called Spinosum). The experimental charge/dimer is 1.49 rather than 2.0 with 0.59 molecules of anhydrogalactose rather than one. The three-dimensional structure of the -carrageenan double helix has been determined [247] as forming a half-staggered, parallel, threefold, right-handed double helix, stabilized by interchain O2-H . . . O-5 and O6-H . . . O-2 hydrogen bonds between the .beta.-D-galactopyranose-4-sulfate units. The idealized structure of .lamda.-carrageenan (lambda-carrageenan) is: -(1.fwdarw.3)-.beta,-D-galactopyranose-2-sulfate-(1.fwdarw.4)-.alpha.-.-D-galactopyranose-2,6-disulfate-(1.fwdarw.3) carrageenan (isolated mainly from *Gigartina pistillate* or *Chondrus crispus*) is converted into .theta.-carrageenan (theta-carrageenan) by alkaline elimination, but at a much slower rate than causes the production of -carrageenan and .kappa.-carrageenan. The experimental charge/dimer is 2.09 rather than 3.0 with 0.16 molecules of anhydrogalactose rather than zero. The biocompatible hydrogel can be substantially free of sulfated oligosaccharides. Thus, the biocompatible hydrogel can be substantially free of sulfated cyclic sugars. Thus, the biocompatible hydrogel can be substantially free of sulfated cyclooextrins.

The biocompatible hydrogel can also comprise at least one other biocompatible polymer. For example, the at least one other biocompatible polymer can comprise hyaluronic acid, heparin, a heparin fragment, glycosaminoglycans, glycosylated proteins (proteoglycans), glycosylated non-degradable and degradable synthetic polymers, polymers with sugar residues, or a combinations thereof.

The at least one other biocompatible polymer can comprise a self-assemble peptide. Certain peptides are able to self-assemble into stable hydrogels at low (0.1-1%) peptide concentrations (Zhang S, et al, 1993; Zhang S, et al, 1995; Holmes T C, et al, 2000). Such self-assembling peptides are characterized by amino acid sequences of alternating hydrophobic and hydrophilic side groups. Sequences of charged amino acid residues include alternating positive and negative charges (Zhang S, et al, 1993; Zhang S, et al, 1995; Holmes T C, et al, 2000). Self-assembling peptides form stable .beta.-sheet structures when dissolved in deionized water. Exposure to electrolyte solution initiates .beta.-sheet assembly into interweaving nanofibers. Such self-assembly occurs rapidly when the ionic strength of the peptide solution exceeds a certain threshold, or the pH is such that the net charge of the peptide molecules is near zero (Caplan M R, et al, 2000). Intermediate steps of self-assembly have been investigated by observing relatively slow nanofiber formation and subsequent network assembly in deionized water, without triggering rapid self-assembly by the addition of electrolytes (Marini D M, et al, 2002). The self-assembling peptide hydrogel contains unique features for a tissue engineering polymer scaffold. The nanofiber structure is almost 3 orders of magnitude smaller than most polymer microfibers and presents a unique polymer structure with which cells may interact. In addition, peptide sequences may be designed for specific cell-matrix interactions that influence cell differentiation and tissue formation (Holmes T C., 2002). For example, self-assembling peptide KLD-12 hydrogel has been studied as a 3D scaffold for encapsulation of chondrocytes (Kisiday et al, 2002).

The biocompatible hydrogel can further comprise block copolymers such as PLURONICS™ (also known as POLOXAMERS™), which are poly(oxyethylene)-poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

Thus, in another aspect, the average pore size in the biocompatible hydrogel is less than about 10 nm, less than about 50 nm, less than about 100 nm, less than about 200 nm, less than about 300 nm, less than about 400 nm, less than about 500 nm, less than about 600 nm, less than about 700 nm, less than about 800 nm, less than about 900 nm, or less than about 1000 nm. Thus, the average pore size can be from about 1 .mu.m to 10 nm, from about 1 .mu.m to 50 nm, from about 1 .mu.m to 100 nm, from about 1 .mu.m to 200 nm, from about 1 .mu.m to 300 nm, from about 1 .mu.m to 400 nm, from about 1 .mu.m to 500 nm, from about 1 .mu.m to 600 nm, from about 1 .mu.m to 700 nm, from about 1 .mu.m to 800 nm, from about 1 .mu.m to 900 nm, or from about 1 .mu.m to 1000 nm.

The biocompatible hydrogel of the provided method can have a high elastic modulus. For example, the modulus can be greater than 0.001, 0.05, 0.01, 0.1, 0.2, 0.3, 0.4, 0.5, 0.6, 0.7, 0.8, 0.9, 1, 2, 3, 4, 5, 6, 7, 8, 9, 10, 15, 20, 50 megapascals. Compositions such as sodium alginate that can be used to increase the modulus of the biocompatible hydrogel are known in the art.

In one aspect, the elastic modulus is determined in part by the concentration of the biocompatible hydrogel, such as agarose. Thus, as an example, wherein the biocompatible hydrogel is agarose, the concentration of agarose can be at least about 1%, 2%, 3%, 4%, 5%, 6%, 7%, 8%, 9%, 10%, 11%, 12%, 13%, 14%, 15%, 16%, 17%, 18%, 19%, 20%, or higher.

An elastic modulus, or modulus of elasticity, is the mathematical description of an object or substance's tendency to be deformed when a force is applied to it.

The concept of a constant elastic modulus is dependent on the assumption that the stress-strain curve is always linear. In reality, the curve is only linear within certain limits, because an object stretched or compressed too far will break, and an object under high pressure may undergo processes that will affect the stress-strain curve, such as chemical reactions or buckling. Thus, there are three primary elastic moduli, each describing a different kind of deformation. They are Young's modulus, modulus of rigidity, and bulk modulus. Young's modulus (E) describes tensile elasticity, or the tendency of an object to deform along an axis when opposing forces are applied along that axis; it is defined as the ratio of tensile stress to tensile strain. Because all other elastic moduli can be derived from Young's modulus, it is often referred to simply as the elastic modulus. Young's modulus is a mathematical consequence of the Pauli exclusion principle. The shear modulus or modulus of rigidity (G) describes an object's tendency to shear (the deformation of shape at constant volume) when acted upon by opposing forces; it is defined as shear stress over shear strain. The shear modulus is part of the derivation of viscosity. The bulk modulus (K) describes volumetric elasticity, or the tendency of an object's volume to deform when under pressure; it is defined as volumetric stress over volumetric strain, and is the inverse of compressibility. The bulk modulus is an extension of Young's modulus to three dimensions.

The invention may also be practiced with other release systems which have been described. Some non-limiting examples of such systems include Hyaluronan (Hyaff-11), PGA-scaffold, type II collagen-glycosaminoglycan scaffold, glycerol tripalmitate, OPF and gelatine microparticles, PEO-hydrogels with PLGA microspheres, OPF and gelatine microparticles, Collagen/chitosan/glycosaminoglycan with or without chitosan microspheres, P(NiPAAm-co-AAC)/HA hydrogels, Collagens, PLA-PEG/IP-CHA and Gelatine/chondroitin/hyaluronate with or without gelatine microparticles.

The invention may also be practiced with other release systems which have been described, Some non-limiting examples of such systems include microspheres, liposomes, alone or in combination with the above described biogels and hydrogels.

The invention therefore relates to a method as described above wherein said biogel is selected from the group consisting of a hydrogel, a saccharide polymer, agarose, Carrageenans, Hyaluronan (Hyaff-11), PGA-scaffold, type II collagen-glycosaminoglycan scaffold, glycerol tripalmitate, OPF and gelatine microparticles, PEO-hydrogels with PLGA microspheres, OPF and gelatine microparticles, Collagen/chitosan/glycosaminoglycan with or without chitosan microspheres, P(NiPAAm-co-AAC)/HA hydrogels, collagens, PLA-PEG/IP-CHA and Gelatine/chondroitin/hyaluronate with or without gelatine microparticles All the drug release systems described above and combinations hereof have been described to release these factors to aid cartilage repair and prevent further degeneration. However, the site of delivery of the pharmaceutically active agents according to the teachings of the prior art are always in the affected tissue, such as in the case of an affected joint, mostly in the joint space.

The invention now provides for a superior delivery system by injecting these drugs into the fat-pad of the affected joint.

If injected in the joint space, the motion of the joint may affect the physical integrity of the release systems and thereby the release characteristics. In turn the mechanical characteristics and degeneration (products) of these release systems may negatively affect the adjacent articular cartilage.

If injected straight into the Fat pad, a depot containing drugs that are not enclosed in a carrier matrix (such as the biogel or other depot-structures) may present a very high concentration of drugs at the site of injection, which in turn can damage or kill the surrounding tissue at the site of the injection. As a consequence the injection of non-enclosed drugs may negatively affect the joint and the surrounding tissue.

This study shows that implantation (e.g. by injection) of a drug release system in the fatpad which is situated intra-articular or the fatpad adjacent to the joint (in particular Hoffa's fatpad in the knee joint) gives superior release characteristics compared to currently used injections in the joint space.

In conclusion, we have shown that injection of a Bio-Gel in Hoffa's fatpad is achieved easily and in reproducible manner. Fluoroscopy showed in both human and rat knees that the gel is retained in the fatpad and gives a controlled release of contrast agent. The osteoarthritic changes after injection of MIA were significant partially inhibited and/or reversed after injection of a Bio-Gel with a COX-2 inhibitor, whereas injection of a Bio-Gel only did not inhibit progression of OA. Cartilage repair, using techniques such as MACI and microfracturing, is significantly improved by controlled release of a COX-2 inhibitor from Hoffa's fatpad.

REFERENCES

1. Aroen, A., S. Loken, S. Heir, E. Alvik, A. Ekeland, O. G. Granlund, and L. Engebretsen. Articular cartilage lesions in 993 consecutive knee arthroscopies. Am J Sports Med. 32(1). 211-5, 2004
2. Curl, W. W., J. Krome, E. S. Gordon, J. Rushing, B. P. Smith, and G. G. Poehling. Cartilage injuries: a review of 31,516 knee arthroscopies. Arthroscopy. 13(4). 456-60, 1997
3. Gelber, A. C., M. C. Hochberg, L. A. Mead, N. Y. Wang, F. M. Wigley, and M. J. Klag. Joint injury in young adults and risk for subsequent knee and hip osteoarthritis. Ann Intern Med. 133(5). 321-8, 2000
4. Hardaker, W. T., Jr., W. E. Garrett, Jr., and F. H. Bassett, 3rd. Evaluation of acute traumatic hemarthrosis of the knee joint. Soutn Med J. 83(6). 640-4, 1990
5. Hjelle, K., E. Solheim, T. Strand, R. Muri, and M. Brittberg. Articular cartilage defects in 1,000 knee arthroscopies. Arthroscopy. 18(7). 730-4, 2002
6. Hunziker, E. B. and L. C. Rosenberg. Repair of partial-thickness defects in articular cartilage: cell recruitment from the synovial membrane. J Bone Joint Surg Am. 78(5). 721-33, 1996
7. Mankin, H., V. Mow, and J. Buckwalter, Articular cartilage repair and osteoarthritis. Biology and Biomechanics of the Musculoskeletal System, ed. J. Buckwalter, T. Einhorn, and S. Simon. Rosemont: American Academy of Orthopaedic Surgeons, 2000
8. Noyes, F. R., R. W. Bassett, E. S. Grood, and D. L. Butler. Arthroscopy in acute traumatic hemarthrosis of the knee. Incidence of anterior cruciate tears and other injuries. J Bone Joint Surg Am. 62(5). 687-95, 757, 1980
9. Sangha, O. Epidemiology of rheumatic diseases. Rheumatology (Oxford). 39 Suppl 2. 3-12, 2000

EXAMPLES

Example 1

Injection of a Gel in Hoffa's Fat-Pad for Controlled Release of Pro Chondrogenic Factors Rat model: Dutch laws on animal experimentation were strictly followed throughout the study and the experimental animal protocol was approved by the Maastricht University committee for animal experiments. After induction of general anaesthesia, both knees of Wistar rats were shaved and prepared for aseptic surgery. The centre of the patella tendon was identified. A 28 G needle with a 1 ml syringe was used to penetrate the centre patella tendon. Directly after the patella tendon was penetrated, approximately between 0.1 and 0.2 ml of the Bio-Gel containing iodine based contrastagent (Visipaque®) was injected in Hoffa's fat-pad (HFP). Since the gel was mixed with X-ray contrast, the side of injection was examined by fluoroscopy.

Example 2

Ex Vivo Infection and Release from Hoffa's Fatpad

Figure 1:
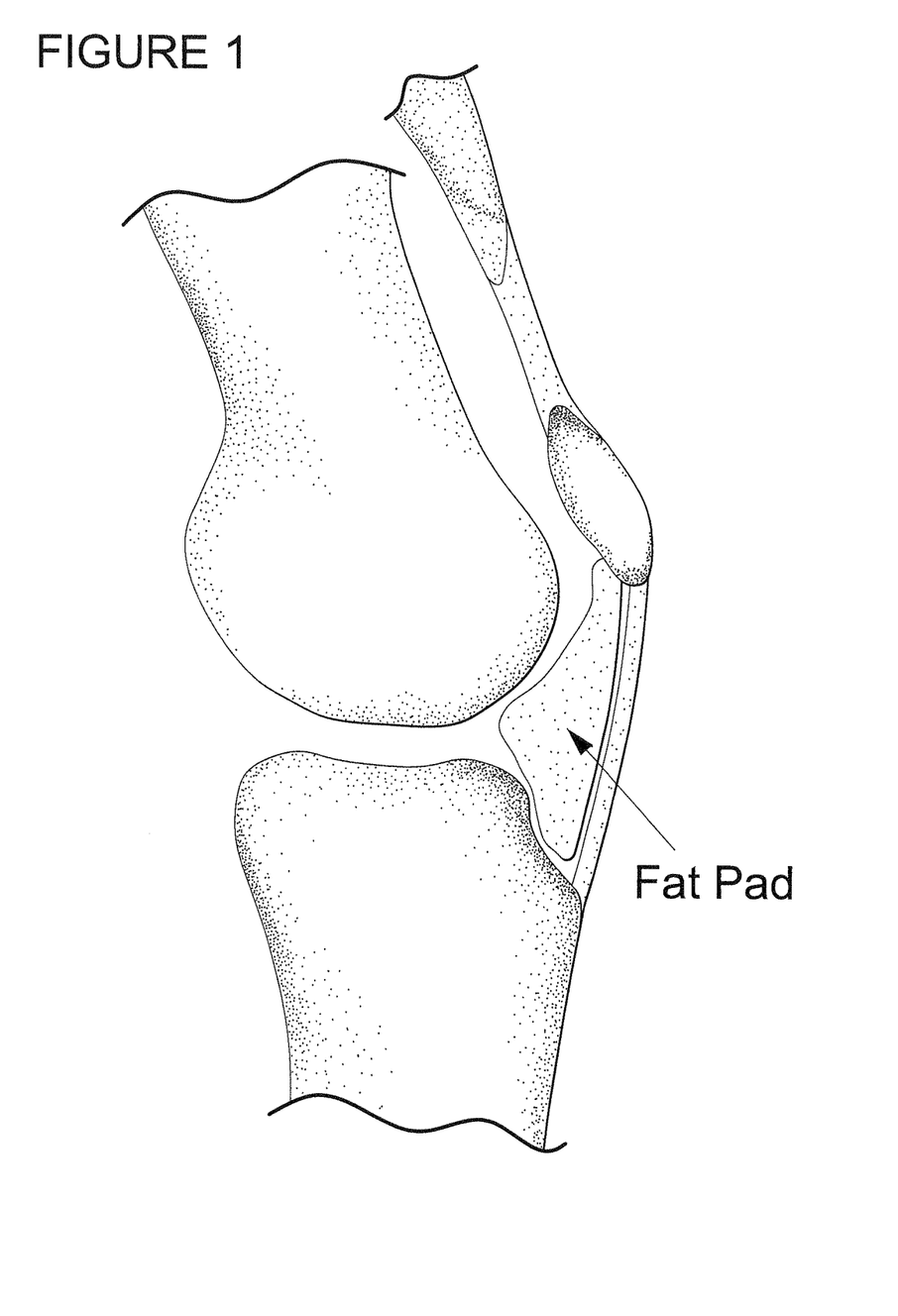
FIG. 1: Schematic representation of a knee joint showing the position of the Hoffa fat pad.
Figure 2:
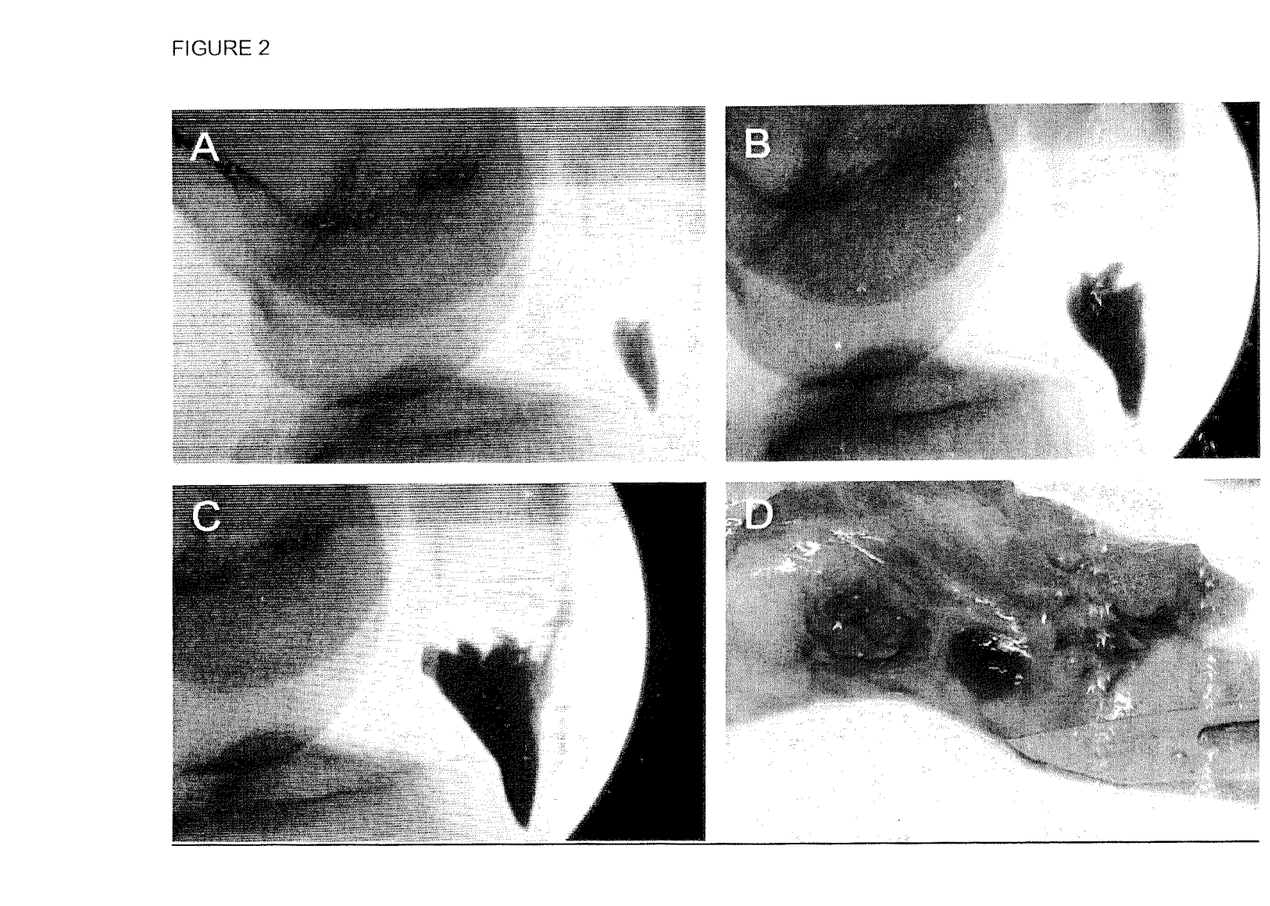
FIG. 2: (A) Injection of 1 mL, (B) 3 mL, and (C) 5 mL in Hoffa in a cadaver human knee joint. Note that even after 100 flexion extension cycles (C) the contrast agent is still maintained in Hoffa's fat pad. (D) Injection of 2 depots of In—GelI™ in Hoffa. Note that the blue dye is contained within the gel.

It is advantageous that injection in HFP is feasible, a certain amount can be injected, the injected gel is contained in Hoffa's fatpad, and a certain release is maintained in time. For this purpose we injected different amounts of a radiopaque contrast agent in human HFPs. The HFP could easily be reached through the patellar tendon. An amount of 10 cc could be injected in HFP. Within HFP the contrast agent was not contained in one depot but distributed equally through the fatpad (FIG. 2). For an ex vivo approach HFPs were collected after TKA. The freshly harvested HFPs were injected with bromophenol blue in InGell™. These studies show that at 37° C. gel formation was instantaneous, and the dye is maintained in InGell™ (FIG. 2D). In contrast, injections of the colour dye or contrast agent without the Bio-Gel showed immediate and complete dispersion throughout the Hoffa, with no containment of the additives at all (FIG. 2A-C). Diffusion from InGell™ was confirmed by spectrophotometric analysis of the medium during the first days after injection.

Example 3

Histological Evaluation

Five days and 30 days post-injection the rats were sacrificed and whole knee joints were fixed in 4% buffered formalin and decalcified in 10% EDTA for histology. After embedding in paraffin 7 µm sections were cut and stained with hematoxylin/eosin or with safarin O/fast green.

Both fluoroscopy and histology showed that after penetration of the patella tendon a Bio-Gel could easily and reproducibly be injected in Hoffa's fatpad. Histology and fluoroscopy showed retention of the Bio-Gel in Hoffa's fatpad even after 30 days follow-up. The human cadaver study confirmed this finding; after 1000 flexion/extension cycles the Bio-Gel remained in Hoffa's fatpad.

Example 4

Injection of a Bio-Gel Containing a COX-2 Inhibitor in Hoffa's Fatpad

After induction of general anaesthesia, both knees of Wistar rats were shaved and prepared for aseptic surgery. The centre of the patella tendon was identified. A 28 G needle with a 1 ml syringe was used to penetrate the centre patella tendon. Directly after the patella tendon is penetrated and 0.1 ml of the Bio-Gel containing 500 µg of Parecoxib was injected in Hoffa's fad pad. Directly after injection, 1 day, 5 days, 10 days and 30 days after injection the rats were sacrificed. The synovial joint fluid (SJF) was removed and the and whole knee joints were fixed in 4% buffered formalin and decalcified in 10% EDTA for histology. After embedding in paraffin 7 µm sections were cut and stained with hematoxylin/eosin or with safarin O/fast green.

The concentration of parecoxib in the SJF was examined using a high-performance liquid chromatography Histological evaluation showed a decreased volume of the gel in Hoffa's fatpad and no presence of the Bio-Gel itself in the adjacent joint-space and surrounding tissues (e.g. synovial membrane). Parecoxib levels in the SJF increased to a maximum level at 1 day after injection. Even after 30 days follow the intra-articular level of parecoxib remained stable.

Histological evaluation showed several macrophages and some small giant-cells surrounding the Bio-Gel containing the COX-2 inhibitor indicating only a minor inflammatory response.

Example 5

Prevention of OA by Controlled Release of a COX-2 Inhibitor

OA model: The rat Monoiodoaceticacid (MIA) OA model described by Guingamp et al. was used for this study. 3-month old Wistar rats were used (body weight 220-240 g) were anesthetized, after shaving the knee, the skin was disinfected and a lateral parapatellar injection of 6 mg MIA (60 mg/ml) using a 28 G needle. In controls a 0.9% NaCl injection was given.

COX-2 inhibitor injection: Directly after or 7 days after MIA injection, the centre of the patella tendon is identified. A 28 G needle with a 1 ml syringe is used to penetrate the centre patella tendon. Directly after the patella tendon is penetrated 0.1 ml of Bio-Gel containing 500 µg Parecoxib® is injected in Hoffa's fat-pad. As control 0.1 ml of Bio-Gel only is injected in Hoffa's fatpad.

30 days after injection of MIA, rats were sacrificed. At this time and one half of the whole knee joints were fixed in 4% buffered formalin and decalcified in 10% EDTA for 2 weeks. After embedding in paraffin 7 µm sections were cut and stained with safarin O/fast green and thionine. For immunohistochemical staining of Collagen Type II, sections were de-paraffinized and hydrated using standard protocols. Then the sections were pre-treated with 1% Hyaluronidase (30 minutes 37° C.) and 0.2% pronase (30 minutes 37° C.) and a 1:50 dilution in PBS of the primary antibody, mouse-monoclonal anti Collagen Type II (II-II6B3, DSHB, Iowa, USA), solution was applied. After overnight incubation with the primary antibody at room temperature, sections were washed with PBS and incubated with the secondary antibody Rabbit anti-mouse IgG-HRP (ITK diagnostics, The Netherlands). Subsequently, sections were washed with PBS and incubated with the avidin-biotin complex conjugated with Horseradish Peroxidase (HRP). Diaminobenzidine (DAB) was used as a substrate for peroxidase. Mankin scores for OA grading were scored by 2 blinded individuals.

Example 6

Protein Isolation and mRNA Isolation

From the other half of the joint the cartilage was resected and immediately after harvest, the tissue was frozen in liquid nitrogen and pulverized. For mRNA isolation, the resulting powder collected in TriZol reagent. Total RNA was extracted, cDNA synthesized, and RT-qPCR was performed in triplicate for Collagen Type I, II and X, RunX2, Aggrecan, Vascular Endothelial Growth Factor (VEGF), Hypoxia Inducible Factor (HIF)-1α IS HlF1alpha relevant hier? using previously published primer sequences and normalized to 28S rRNA. The mRNA quantification was carried out using a ABI PRISM® 7700 Sequence Detection System (Applied Biosystems, Foster City, Calif., USA, user bulletin #2). Serially diluted standard curves were included to quantify the samples. PCR conditions were: 2 min at 50° C., 10 min at 95° C., 40 cycles for 15 s at 95° C. and 1 min at 60° C. followed by a melt curve 15 s at 95° C. ramp to 60° C. for 1 min, followed by 20 s at 95° C. Data were analyzed using Sequence Detection Software version 1.7 (Applied Biosystems, Foster City, Calif., USA).

Similarly, for Western analysis, the powder was lysed using standard RIPA buffer and samples were homogenized by sonication, followed by centrifugation (13.000×g; 4° C.) to remove insoluble material. Total protein concentration in the purified lysate was determined using the BCA assay (Sigma-Aldrich). Ten microgram total protein was loaded per sample and separated by SDS-PAGE and the protein bands were transferred to nitrocellulose membranes by electroblotting. Immunodetection of Collagen type II and X, RunX2, and Tubulin was achieved using primary antibodies recognizing type II collagen (Southern Biotechnology Associates Inc., Birmingham, USA). Collagen type X (Calbiochem), RunX2 (MBL) and α-Tubulin (Sigma-Aldrich), respectively, followed by HRP-conjugated polyclonal swine-anti-rabbit, rabbit-anti-goat and rabbit-anti-mouse secondary antibodies, respectively (Dako, Glostrup, Denmark). Bound antibodies were visualized by enhanced chemiluminescence using hyperfilm (GE Healthcare, Den Bosch, The Netherlands).

Mankin scores showed that the level of OA was significantly lower after injection of the Bio-Gel containing a COX-2 inhibitor. PCR data, Western blot and immunohistochemistry confirmed these data; collagen type II levels where lower after injection of the Bio-Gel only compared to collagen type II levels after injection of a BIO-GEL containing COX-2 inhibitors in Hoffa's fatpad.

Furthermore, markers known to be upregulated during OA such as RunX2 and Collagen type X were significantly higher after injection of a Bio-Gel only.

Example 7

Enhanced Cartilage Repair with Controlled Release of a COX-2 Inhibitor

Surgical procedure: Skeletally mature Dutch milk goats were used for this study. During the first operation, both knee joints of the goats were opened using a medial parapatellar incision. Using a 8 mm in diameter dermal punch a cartilage only defect was created on both medial femoral condyles. The cartilage of both sides was minced and after an overnight collagenase treatment, cells were isolated and expanded in monolayer.

After 4 weeks a cell number of approximately $10 \times 10^6$ cells was reached. Consequently these cells were seeded and allowed to attach in a collagen carrier for 24 hrs as described earlier as Matrix-supported Autologous Chondrocyte Implantation (MACI). Hereafter a second operation was performed. The knee joints were opened and one the cartilage defect of one knee joint was repaired using the MACI method. The defect in the other knee joint was repaired using microfracturing as described by Steadman et al. In 10 goats Hoffa's fatpad was injected (as described earlier) with a Bio-Gel containing 1.5 mg of Parecoxib, in 10 goats Hoffa's fatpad was injected (as described earlier) with a Bio-Gel only, and in 10 goats no injection was performed.

Goats were allowed full-weight bearing after both surgical procedures.

Histological evaluation: 3 months after the second operation, goats were sacrificed. At this time the medial condyle was fixed in 4% buffered formalin and decalcified in 10% EDTA for 2 weeks. After embedding in paraffin 7 µm sections were cut and stained with safarin-O/fast green and thionine. For immunohistochemical staining of Collagen Type II, sections were de-paraffinized and hydrated using standard protocols. Then the sections were pre-treated with 1% Hyaluronidase (30 minutes 37° C.) and 0.2% pronase (30 minutes 37° C.) and a 1:50 dilution in PBS of the primary antibody, mouse-monoclonal anti Collagen Type II (II-II6B3, DSHB, Iowa, USA), solution was applied. After overnight incubation with the primary antibody at room temperature, sections were washed with PBS and incubated with the secondary antibody Rabbit anti-mouse IgG-HRP (ITK diagnostics, The Netherlands). Diaminobenzidine (DAB) was used as a substrate for peroxidase. Mankin scores for OA grading and O'Driscoll scores for cartilage repair were scored by 2 blinded individuals.

O'Driscoll cartilage repair scores were significantly better after injection of a Bio-Gel containing a COX-2 inhibitor. Cartilage repair scores were comparable between the Bio-Gel only group and the group in which no injection was done. After 3 months follow-up, there was no significant difference between the MACI treated defects and the microfracture treated defects.

Although not significantly better, Mankin scores indicated less OA features (e.g. number of tidemarks and surface fibrillation) after injection with the Bio-Gel containing a COX-2 inhibitor in Hoffa's fatpad.

Example 8

Injection of a Stereocomplex Gel Containing rhIL-2 Into Mice Tumour Models

G. W. Bos et al (European Journal of Pharmaceutical Chemistry 21(2004), 561-567), Hiemstra et al (Biomacromolecules, 2006, 7, 2790-2795) described injections of a thermo reversible gel formulations containing paclitaxel. KIM et al (Arch. Pharm. Res. 25, 229 (2002) have demonstrated the feasibility of injecting stereo-complex gels or thermo reversible gels to form a drug depot in a fatty tissue environment subcutaneously. From that environment the drugs were released and transported systemically. Injections of the liquid formulations containing amphiphilic IL-2 or hydrophobic paclitaxel were given subcutaneously, using syringes with medium (14 G) to thin needles (23 G). Within a short term depots were formed. Diffusion-based release of the actives was observed between days to weeks, directly or indirectly, and therapeutic efficacy in both metastasised tumour mice models and in prostate cancer in humans (Kim et al.) was witnessed.

In other examples we demonstrate the injection and containment of contrast agent inside the Hoffa. In yet other experiments (Weinands/van Osch et al) the release and diffusion of various cytokines and growth factors from the Hoffa into the synovial cavity has been demonstrated. These independent experiments make it plausible and deductible to those skilled in the art that biogels containing different actives which can be release through diffusion and or degradation will be release from the Hoffa in to the synovium In a particular useful embodiment of the invention, a method is provided for protecting surrounding tissue in a fat pad against high doses of drugs as a consequence of forming a drug depot in situ, by encapsulating the drugs in a carrier injected into the fat pad.

The invention claimed is:

1. A method for improving cartilage repair in a joint of a subject in need thereof comprising administering directly into the fat pad of said joint a COX-2 inhibitor in an amount sufficient to effect said improvement.

2. The method according to claim 1 wherein said COX-2 inhibitor is contained in a device suitable for controlled release of said COX-2 inhibitor.

3. The method according to claim 2 wherein said device is a biogel.

4. The method according to claim 3 wherein said biogel comprises a biocompatible polymer.

5. The method according to claim 3 wherein said biogel is biodegradable.

6. The method according to claim 3 wherein said biogel is selected from the group consisting of a hydrogel, a saccharide polymer, microspheres, liposomes, agarose, Carrageenans, Hyaluronan (Hyaff-11), PGA-scaffold, type II collagen-glycosaminoglycan scaffold, glycerol tripalmitate, OPF and gelatine microparticles, PEO-hydrogels with PLGA microspheres, OPF and gelatine microparticles, Collagen/chitosan/glycosaminoglycan with or without chitosan microspheres, P(NiPAAm-co-AAC)/HA hydrogels, collagens, PLA-PEG/IP-CHA and Gelatine/chondroitin/hyaluronate with or without gelatine microparticles.

7. The method according to claim 1 wherein said subject is a human.

8. The method according to claim 1 wherein said joint is a shoulder, elbow, wrist, ankle or hip.

* * * * *